United States Patent [19]

Shoesmith

[11] Plant 4,280

[45] Jul. 18, 1978

[54] CHRYSANTHEMUM PLANT

[75] Inventor: Leonard H. Shoesmith, Westfield-Woking, England

[73] Assignee: Pan-American Plant Company, West Chicago, Ill.

[21] Appl. No.: 798,089

[22] Filed: May 17, 1977

[51] Int. Cl.[2] ..... A01H 5/00
[52] U.S. Cl. ..... Plt./77
[58] Field of Search ..... Plt./77

*Primary Examiner*—Robert E. Bagwill

*Attorney, Agent, or Firm*—Chas. W. Rummler

[57] ABSTRACT

A distinct variety of chrysanthemum plant of the garden type which has excellent performance as a spring, summer and fall potted plant as well as when grown as a natural season garden plant, characterized by its white medium-sized blooms of decorative flower form which are borne in a clubby spray formation. This plant has a tall, upright habit, requiring some growth retardant when grown as a potted plant, and excellent breaking ability when manually pinched.

2 Drawing Figures

BACKGROUND OF THE NEW PLANT

This chrysanthemum plant originated as a seedling of unidentified parentage and was discovered by me in 1973 among a group of random pollinated plants of a similar kind growing in my breeding facilities at Westfield-Woking, Surrey, England. Because of its attractive white flowers and vigorous upright growth habit, I selected this plant for propagation and test and reproduced it at Westfield-Woking, Surrey, England, by means of cuttings from the original plant. Testing and observation of successive generations of this plant grown in outdoor garden and in greenhouse at Westfield-Woking and at West Chicago, Ill., has shown its distinctive characteristics to hold true from generation to generation and to be firmly fixed. Commercial scale propagation of this new plant is now being done at West Chicago, Ill., and at Cortez, Fla.

DESCRIPTION OF THE DRAWINGS

This new chrysanthemum cultivar is illustrated by the two accompanying drawings, one of which is a full color photographic print showing a potted plant of this variety in full bloom and the other of which is a print of a mechanical photocopy of typical leaves of this plant taken at various stages of maturity. The photograph illustrating this plant was made in Feb. 1977 of a plant grown at West Chicago, Ill.

DESCRIPTION OF THE NEW PLANT

The following is a detailed description of this chrysanthemum cultivar based upon observation of plants grown at West Chicago, Ill., the color designations being according to the R.H.S. Colour Chart published by the Royal Horticultural Society of London, England.

THE PLANT

Origin: Seedling.

Parentage: Unidentified, this plant having been found among random pollinated plants of similar kinds.

Classification:

*Botanic.* —*Chrysanthemum morifolium.*

*Commercial.*—Greenhouse pot plant and outdoor garden chrysanthemum.

Form: Perennnial herbaceous bush.

Height: 5 to 9 inches as a pot plant. 16 to 20 inches as an outdoor garden plant.

Growth: Terminal, vigorous and upright with good strength and sturdiness.

Branching: Normal under natural conditions and with 5 to 8 lateral breaks when manually pinched.

Foliage: Quantity — Abundant, with 8 to 10 leaves per 4 inches of stem.

*Size of leaf.*—Length — $1\frac{1}{4}$ to $3\frac{3}{4}$ inches. Width — $\frac{3}{4}$ to $2\frac{1}{8}$ inches.

*Shape.*—Lanceolate, lobed and deeply serrated.

*Color.*—Upper side — Yellow-Green 147A. Under side — Yellow-Green 147B.

*Surface texture.*—Canescent.

*Venation.*—Pinnately veined.

*Petioles.*—About $\frac{3}{8}$ to $\frac{1}{2}$ inch long.

THE BUD

Form: Globular.

Size:

*Diameter.*—About $\frac{1}{4}$ to $\frac{3}{8}$ inch.

*Depth.*—About $\frac{1}{8}$ to 3/16 inch.

Opening: The bud opens slowly.

Color:

*When phyllaries first divide.*—Yellow-Green 144A.

*When florets begin to unfurl.*—Yellow-White 158A.

Phyllaries: Many in number, borne as involucral bracts on the outside of the receptacle.

*Form.*—Spear-shaped.

*Color.*—Inside and Outside — Yellow-Green 146A.

*Surface texture.*—Pubescent.

Peduncle: Length — About $\frac{1}{2}$ to $\frac{5}{8}$ inch.

*Strength.*—Strong and erect.

*Surface texture.*—Pubescent.

*Color.*—Yellow-Green 148C.

THE FLOWER

Blooming habit: The plant can be flowered the year around with photoperiod control.

*Response.*—7 weeks.

*Recommended flowering.*—March 1 to November 1.

*Natural Season flowering.*—September 26 to October 9.

Blooms:

*Flower type.*—Composite and decorative.

*Size of bloom.*—Medium. Diameter: 1½ to 2½ inches. Depth: ½ to 1 inch.

*Shape.*—Flat when bloom first opens, becoming more hemispherical as bloom matures.

*Borne.*—Singly, as a head of many florets borne on a receptacle and presented in clubby spray or corymbose formation.

*Florets.*—Quantity — Numerous. Form: Generally linear with an obtuse apex.

*Arrangement.*—Several rows of ray florets, generally imbricated.

*Texture.*—Medium firm.

*Appearance.*—Very slight shine.

*Discoloration.*—None.

| Color: | March | October | November |
|---|---|---|---|
| Outer florets: | | | |
| Upper side | 155D | 155D | 155D |
| Under side | 155D | 155D | 155D |
| Inside florets: | | | |
| Upper side | 155B | 155B | 155B |
| Under side | 155B | 155B | 155B |
| General Color Tonality: | 155D when plant is viewed from about 6 feet. | | |

Effect of weather: This plant is not affected by wet or hot weather.

Persistence: The florets hang on and dry.

Fragrance: Typical chrysanthemum.

Lasting Quality:

*On plant.*—3 weeks.

*As cut flower.*—Not recommended.

REPRODUCTIVE ORGANS

Stamens: Number — 5. Arrangement — Syngenesious.

*Filaments.*—About 1/16 to ⅛ inch long. Color: Light Yellow.

*Pollen.*—Color — Yellow.

Pistils: Number — One for each ray and disc floret.

*Styles.*—About ⅛ to 3/16 inch long.

*Stigmas.*—Color — Yellow.

Ovaries: Inferior bicarpellate.

This chrysanthemum cultivar is particularly distinguished by its white, medium sized blooms of decorative flower form which are borne in a clubby spray formation, and by its excellent performance as a spring, summer and fall potted plant and as a natural season garden chrysanthemum. The plant has a tall upright habit, which may require some growth retardant treatment when grown as a potted plant; it has strong stems and abundant medium sized foliage, excellent breaking ability when manually pinced, producing 5 to 8 lateral breaks, and a tolerance of soluble salt conditions.

As a greenhouse pot plant, this chrysanthemum cultivar has a uniform 7-week photoperiodic flowering response, a tendency of its blooms to develop a pink tinge when flowered under cool temperatures, and a lasting quality of about 3 weeks.

I claim:

1. A new and distinct chrysanthemum cultivar substantially as herein shown and described, characterized by its medium sized white blooms which appear in a clubby spray formation, its excellent performance as a spring, summer and fall potted plant and as a natural season garden flower, its uniform 7-week photoperiodic flowering response under greenhouse potted plant culture, its normally tall, upright growth habit, and its tolerance of high soluble salt conditions.

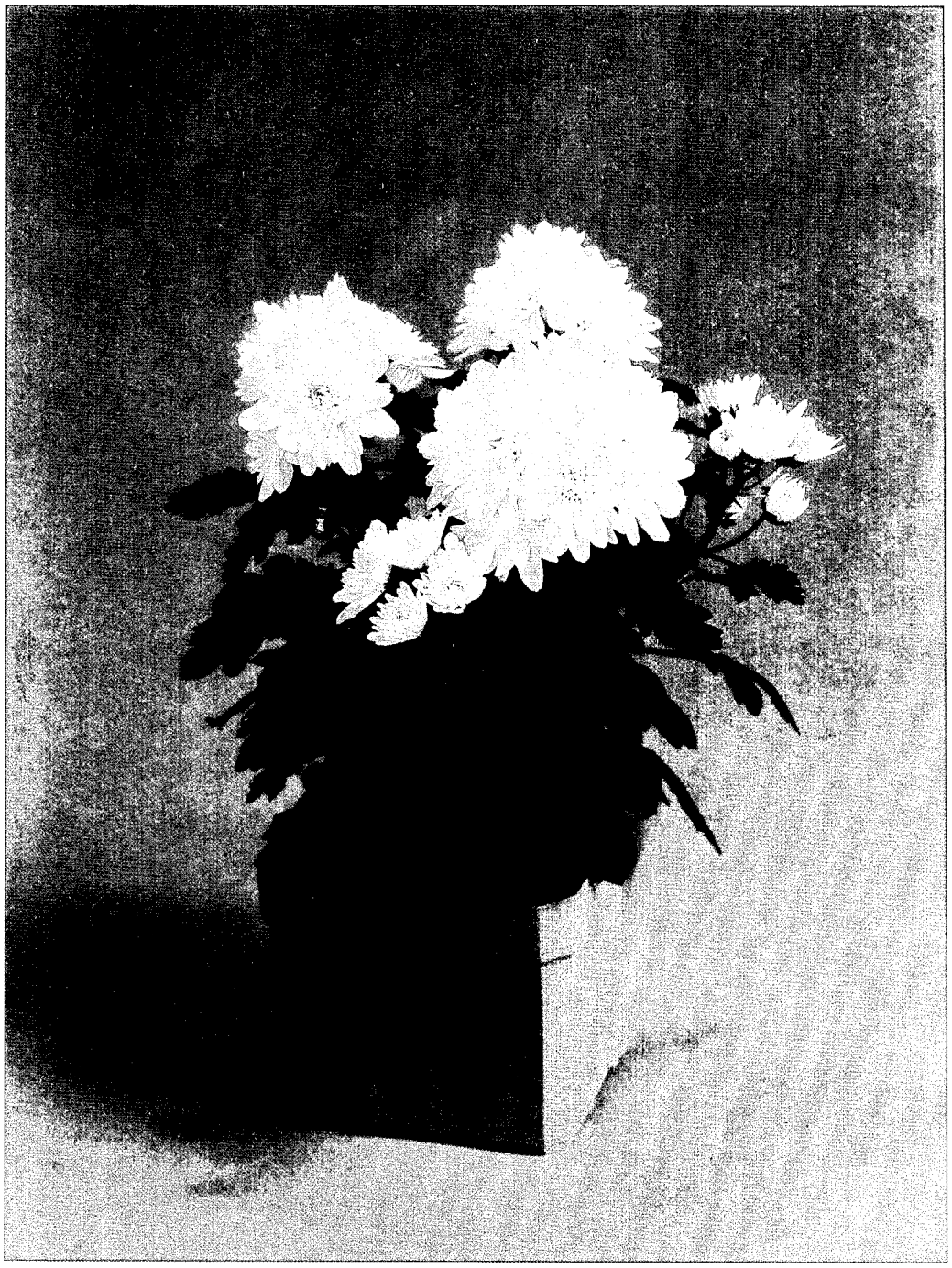

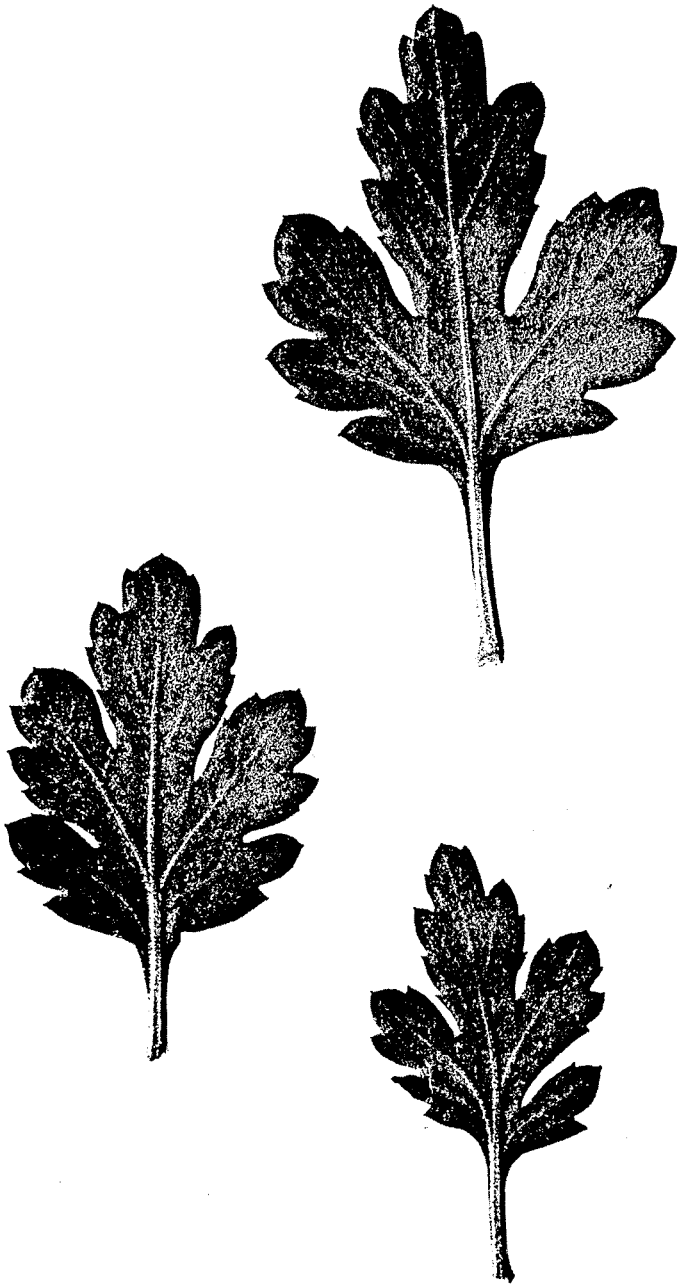

* * * * *